(12) United States Patent
Beekman

(10) Patent No.: US 6,324,258 B1
(45) Date of Patent: Nov. 27, 2001

(54) APPARATUS FOR MAKING TOMOGRAPHIC IMAGES

(75) Inventor: Frederik Johannes Beekman, Utrecht (NL)

(73) Assignee: Academisch Ziekenhuis Utrecht, Utrecht (NL)

( * ) Notice: Subject to any disclaimer, the term of this patent is extended or adjusted under 35 U.S.C. 154(b) by 0 days.

(21) Appl. No.: 09/180,314
(22) PCT Filed: May 12, 1997
(86) PCT No.: PCT/NL97/00264
   § 371 Date: Jul. 19, 1999
   § 102(e) Date: Jul. 19, 1999
(87) PCT Pub. No.: WO97/43667
   PCT Pub. Date: Nov. 20, 1997

(30) Foreign Application Priority Data
May 10, 1996 (NL) ................................................ 1003081

(51) Int. Cl.$^7$ ........................................................ G21K 1/02
(52) U.S. Cl. ........................ 378/145; 378/154; 378/146; 250/363.04; 250/363.1
(58) Field of Search ................ 378/65, 119, 145, 378/146, 147, 156, 153, 154, 155, 203

(56) References Cited

U.S. PATENT DOCUMENTS

| | | | | |
|---|---|---|---|---|
| 2,770,719 | * | 11/1956 | Simjian | 378/145 |
| 4,490,835 | * | 12/1984 | Wons | 378/146 |
| 5,040,202 | * | 8/1991 | Scheid | 378/155 |
| 5,062,129 | * | 10/1991 | Mulder | 378/156 |
| 5,448,611 | * | 9/1995 | Kerjean | 378/65 |

FOREIGN PATENT DOCUMENTS 0 526 970 A2   6/1992 (EP).
WO 95/14244    5/1995 (WO).

OTHER PUBLICATIONS

*Phys. Med. Biol.*, 1992, vol. 37, No. 3, pp. 507–534, "Review of Convergent beam tomography in single photon emission computed tomography".

Patrick Tan, Dale L. Bailey, Steven R. Meikle, Stefan Eberl, Rober R. Fulton and Brian F. Hutton, *The Journal of Nuclear Medicine*, vol. 34, No. 10, Oct. 1993, "A Scanning Line Source for Simultaneous Emission and Transmission Measurements in SPECT".

Michael A. King, PhD, Benjamin M. W. Tsui, PhD, and Tin–Su Pan, PhD, *Journal of Nuclear Cardiology*, vol. 2, No. 6; 513–524 Nov./Dec. 1995 and vol. 3, No. 1; 55–63 Jan./Feb. 1996, "Attenuation compensation for cardiac singe–photon emission computed tomographic imaging: Part 1. Impact of Attenuation and Methods of Estimating Attenuation Maps".

\* cited by examiner

*Primary Examiner*—David P. Porta
(74) *Attorney, Agent, or Firm*—Kinney & Lange, P.A.

(57) ABSTRACT

Disclosed is a tomographic apparatus (100; 200; 300) wherein a camera (10) is provided with a converging collimator (120; 220; 320), and wherein a planar radiation beam makes a scanning movement to move an elongate illumination pattern (125; 225; 325) over the camera (10). In a first embodiment the collimator (120) is a fan beam collimator, and the radiation source (150) is a line-shaped radiation source which is rotatable about its longitudinal axis. In a second embodiment the collimator (220) is a fan beam collimator, and the radiation source (250) is a point-shaped radiation source which is movable along the convergence line (221) of the collimator (220). In a third embodiment the collimator (320) is a cone beam collimator, and the radiation source (350) is a point-shaped radiation source which is rotatable about an axis of rotation (357) which intersects the convergence point (321) of the collimator (320). As a result, a good image sharpness and a good separation of emission and transmission sources is accomplished.

23 Claims, 11 Drawing Sheets

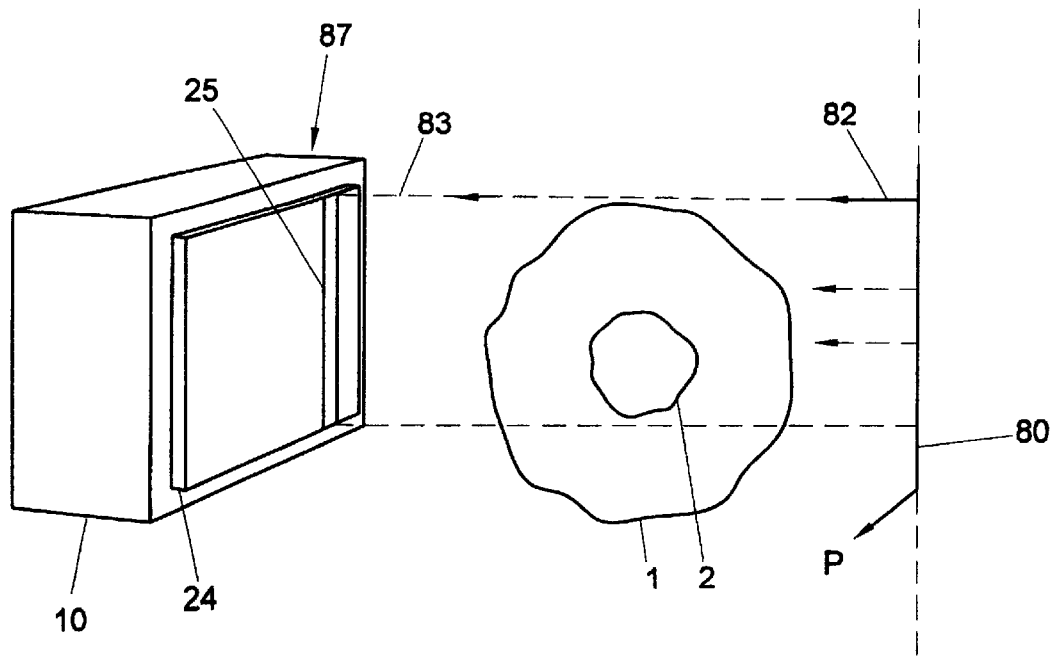
Fig. 4A
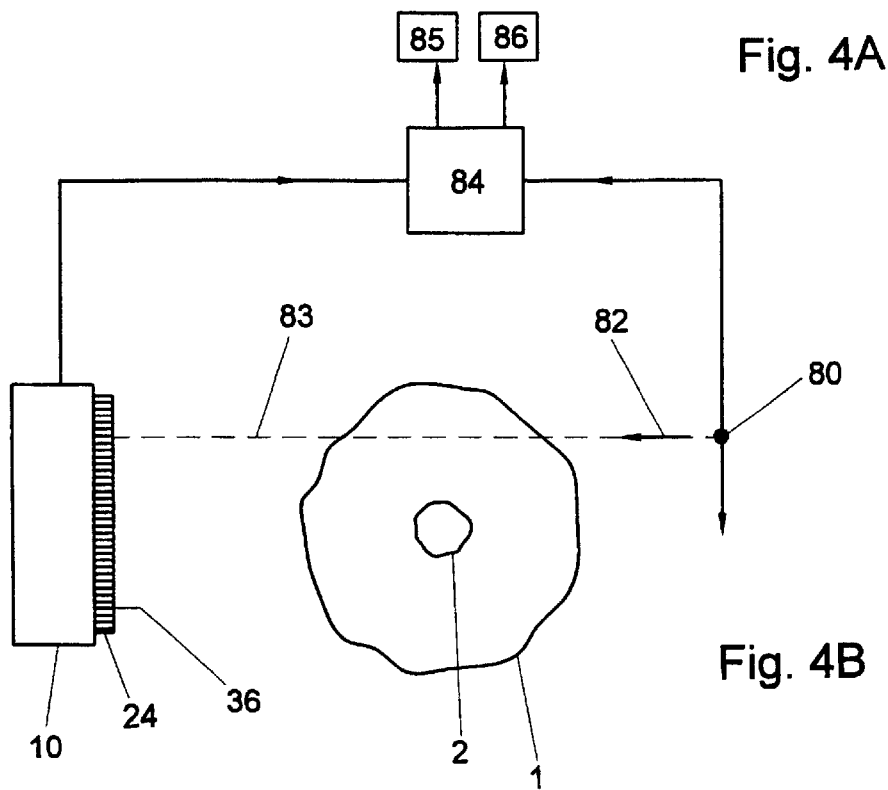
Fig. 4B
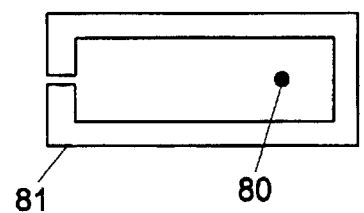

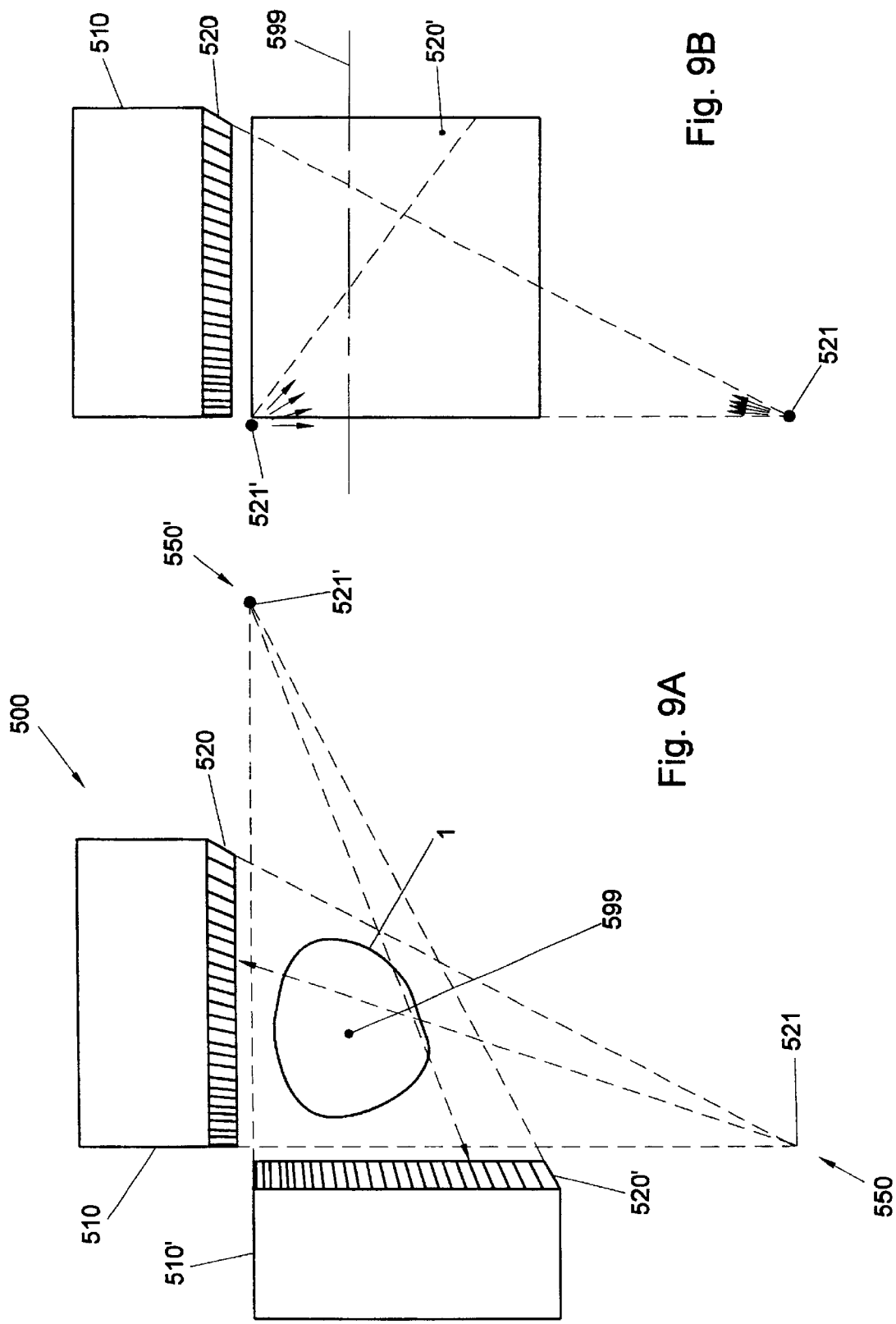

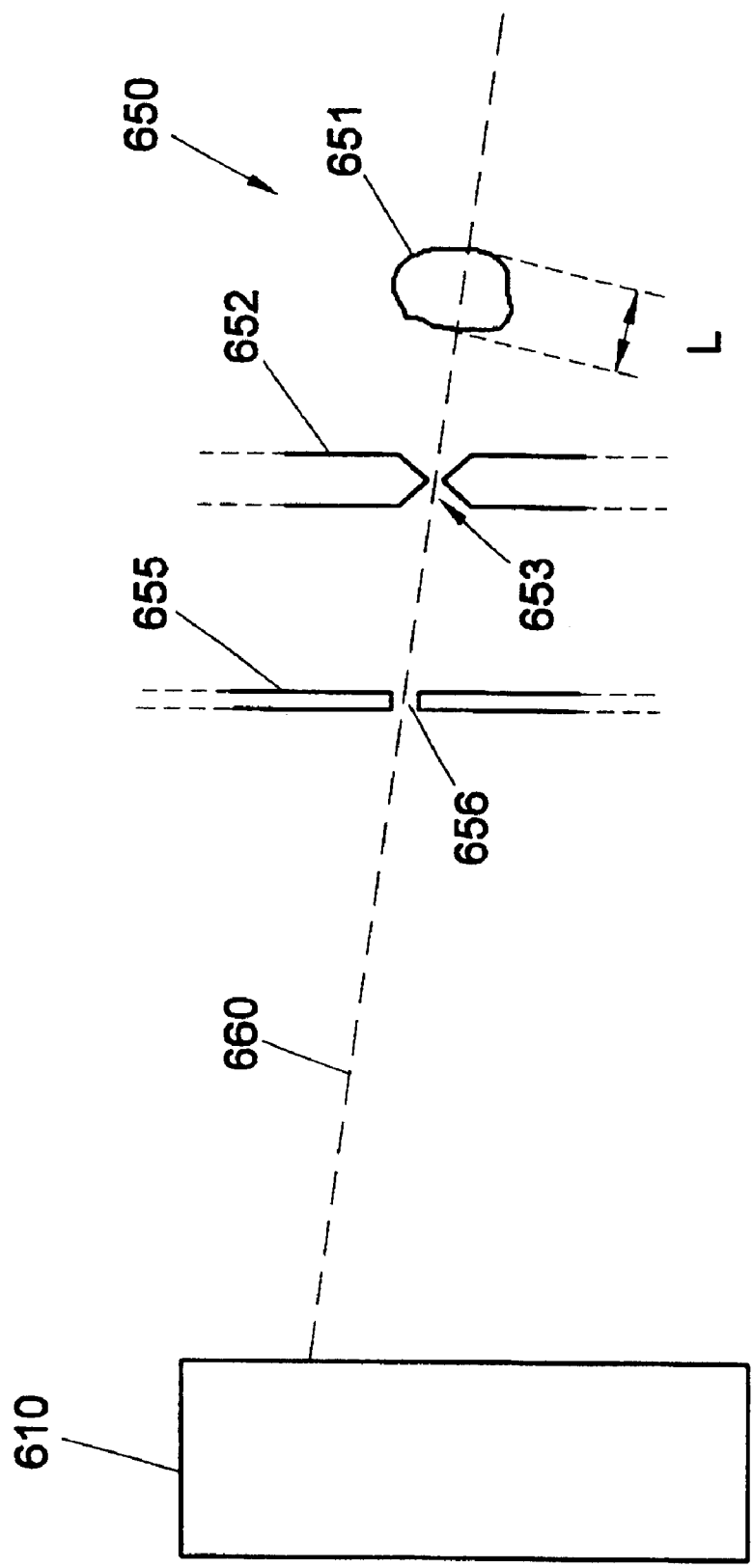

APPARATUS FOR MAKING TOMOGRAPHIC IMAGES

This invention generally relates to the production of tomographic images of an object, normally a person, according to the preamble of claim 1. Since the present invention is of importance in particular for tomographic images obtained by means of gamma radiation, the invention will hereinafter be discussed in particular for this type of radiation. It is noted with emphasis that the principle of the invention is also applicable to the production of images using other kinds of radiation.

In the following, a single recording will be designated by the term "projecton image" (comparable to a photograph). Further, the term "tomography image" or "sectional image" will be used for a reconstructed image of a section of the object, obtained by combining several projection images from different directions.

In principle, tomographic images can be obtained in two different ways. In the first place, it is possible to collect radiation coming from within the object itself, with a detector sensitive to such radiation (camera); such a technique is designated as emission tomography (for instance, SPECT: Single Photon Emission Computed Tomography), and the image obtained is designated as emission projection image. It can be stated in general that an emission projection image provides information about the distribution of radiation-generating matter in the object. When several emission projection images are made, in mutually different directions, it is possible to compute (reconstruct) from the obtained data the concentration distribution of that radiation-generating matter in the object; this is designated as "emission tomography image".

In the second place, it is possible to generate radiation with a radiation source and to direct it towards the object, whereby the radiation that passes through the object is detected with the camera: such a technique is designated as transmission tomography, and the image obtained is designated as transmission projection image. With this technique, therefore, the object is located between the radiation source and the camera. It can be stated in general that a transmission image provides information about the distribution of radiation-attenuating or radiation-absorbing matter in the object. With this technique too, it is possible to combine different transmission projection images to provide a transmission tomography image.

For different reasons it is desired to make emission images and transmission images simultaneously. By this is meant that a camera is simultaneously irradiated with emission radiation coming from the object itself, and with transmission radiation which has passed through the object, while the radiation energy from the external source can be chosen to be different from the radiation energy which is generated in the object itself. An important advantage of such combined recordings is that the transmission tomogram can be used to correct the emission tomogram for attenuation of the radiation in the object.

It is desired to enable discrimination between direct radiation and scattered radiation, so as to be able to obtain better position information. To that end, use is made of a collimator placed before the camera, in combination with a predetermined spatial geometry of the radiation source. The article "Attenuation Compensation for Cardiac Single-Photon Emission Computed Tomography Imaging: Part 1. Impact of Attenuation and Methods of Estimating Attenuation Maps" by M. A. King et al in Journal of Nuclear Cardiology, volume 2, no. 6, November 1995, pp. 513–524, describes examples of this.

Furthermore, the article "A Scanning Line Source for Simultaneous Emission and Transmission Measurements in SPECT" by P. Tan et al in The Journal of Nuclear Medicine, vol. 34, No. 10, October 1993, p. 1752 discloses an apparatus according to the preamble of claim 1. In this article an arrangement is disclosed wherein the line shaped irradiation pattern is moved over the camera. The object of the present invention is to provide a device which on the one hand provides an improved separation between transmission radiation and emission radiation and on the other hand provides an improved image strength in the transmission image, so that the images provided have an improved signal-to-noise ratio over the prior art.

It is a general object of the present invention to provide a tomography device which enables obtaining an emission and a transmission image simultaneously, whereby a good separation between emission and transmission is achieved.

It is a further object of the present invention to provide a tomography device whereby transmission and emission images can be obtained simultaneously in an efficient manner.

It is a still further object of the present invention to provide a tomography device whereby the capacity of the camera is utilized in an efficient manner. These objects are met by an apparatus as defined further in the characterizing portion of claim 1.

EP-A-0 526 970 and U.S. Pat. No. 5,289,008 both disclose an apparatus for making transmission recording of an object during radiation. However, the irradiation pattern is not moved over the camera as required by the present invention.

These and other aspects, features and advantages of the present invention will be clarified by the description hereinbelow of a preferred embodiment of a tomography device according to the invention, with reference to the drawings, in which:

FIG. 4A is a schematic perspective view of a known arrangement for making combined emission/transmission recordings, with a parallel collimator and a moving line source;

FIG. 4B is a schematic top plan view of the arrangement shown in FIG. 4A;

FIGS. 9A and 9B are two schematic mutually perpendicular side elevations of a fifth embodiment of the apparatus according to the present invention for making combined emission/transmission recordings, with two cone beam collimators and two rotary point sources;

FIG. 10 illustrates schematically an improvement, proposed by the present invention, for providing a virtual point source.

Figure 1A:
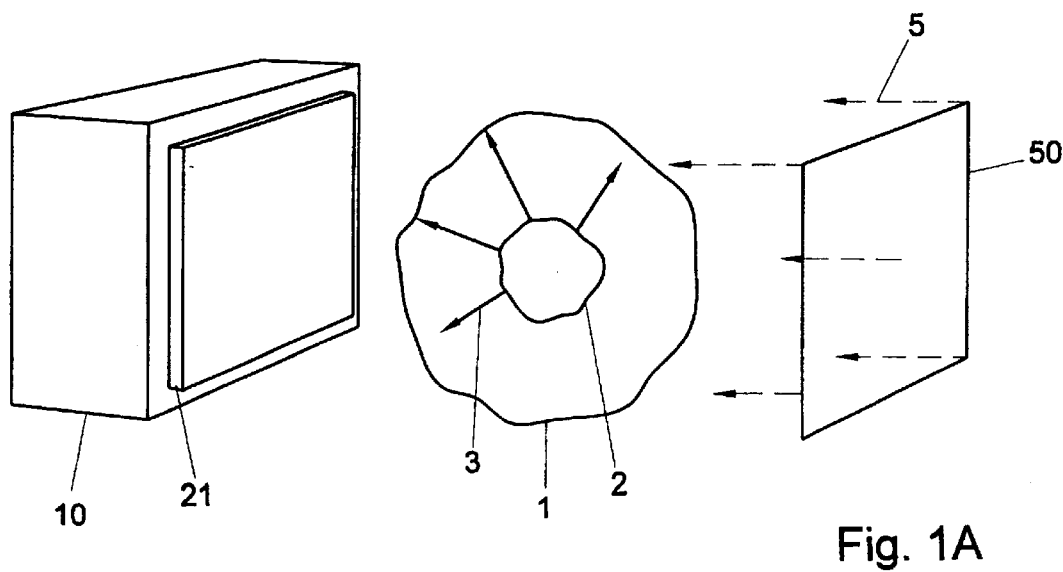
FIG. 1A is a schematic perspective view of a conventional arrangement for making combined emission/transmission recordings, with a parallel collimator and a planar radiation source.

FIG. 1A schematically shows a perspective view of a conventional arrangement for making combined emission/transmission recordings. Arranged on a table (not shown for the sake of simplicity) is an object 1, for instance (a part of) a human being. Located in the object 1 is a portion 2, for instance an organ, to which a radioactive substance has been supplied, so that the portion 2 radiates gamma radiation, as indicated by the arrows 3. It is noted that the portion 2 radiates the radiation 3 in all directions.

Arranged next to the object 1 is a camera 10, which is sensitive to the gamma radiation 3. Since the nature and construction of the camera 10 are not a subject of the present invention, and a knowledge thereof is not necessary for a skilled person to properly understand the present invention, it will not be further described. Suffice it to note that gamma radiation-sensitive cameras are known per se, and that use can be made of such a camera known per se.

Arranged in front of the camera 10 is a collimator 21. A collimator can be regarded, in general, as a transmission means with a direction-selective transmission characteristic, which ensures that a detection segment of the detection surface of the camera 10 can only be irradiated by radiation with a predetermined direction. In one possible embodiment, the collimator 21 is a substantially plate-shaped element of a material with a high degree of absorption, for instance lead, which is provided with a pattern of a multiplicity of bores or passages 31 with a slight diameter, the direction of each passage 31 determining the direction in which the passage can be passed by radiation. In one possible embodiment, the collimator has a thickness of about 2–8 cm, the passages have a diameter of about 2 mm, and the wall portions between adjacent passages have a thickness of about 0.2 mm.

Further, next to the object 1, opposite the camera 10, a radiation source 50 is arranged. The radiation source 50 emits radiation, in this example gamma radiation, as indicated by the dotted arrows 5. The radiation 5 has a particular spatial distribution; in FIG. 1, however, all arrows 5 have been indicated as being mutually parallel, for reasons to be discussed hereinafter.

Generally, the camera 10 with the collimator 21 on the one hand and the radiation source 50 on the other are mounted on a common subframe, which can rotate relative to the table bearing the object 1, for the purpose of obtaining images of the object 1 from different points of view. For the sake of simplicity, this has not been represented in the drawings.

Figure 1B:
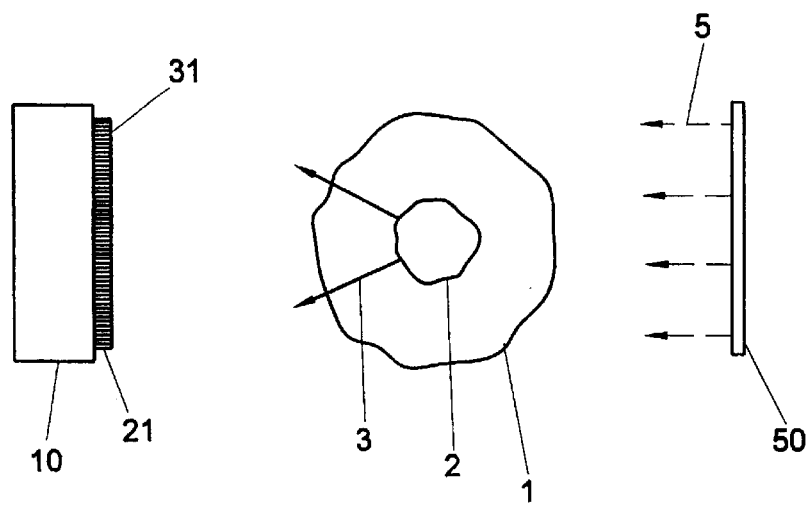
FIG. 1B is a schematic top plan view of the arrangement shown in FIG. 1A.

In the conventional arrangement shown in FIG. 1, the radiation source 50 is a so-called planar source, and the collimator 21 is a parallel collimator, that is, all the passages 31 of the collimator 21 are parallel to each other, as illustrated in FIG. 1B.

An important disadvantage of the combination of a parallel collimator and a planar radiation source is that each surface element of the planar radiation source 50 radiates radiation in all directions within a particular solid angle, but that only a very limited portion is utilized in making the transmission image, namely, only the portion that is directed in the direction of the passages of the collimator 21. Conversely, this implies that a relatively strong source is needed for making a transmission image with a predetermined brightness.

Figure 2A:
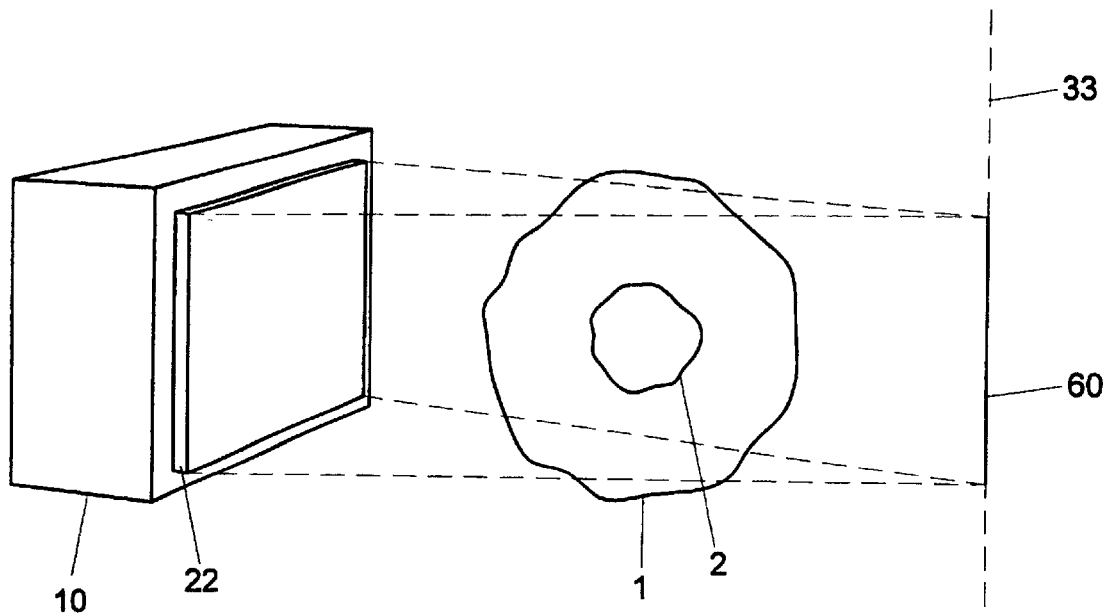
FIG. 2A is a schematic perspective view of a known arrangement for making combined emission/transmission recordings, with a fan beam collimator and a fixed line source.
Figure 2B:
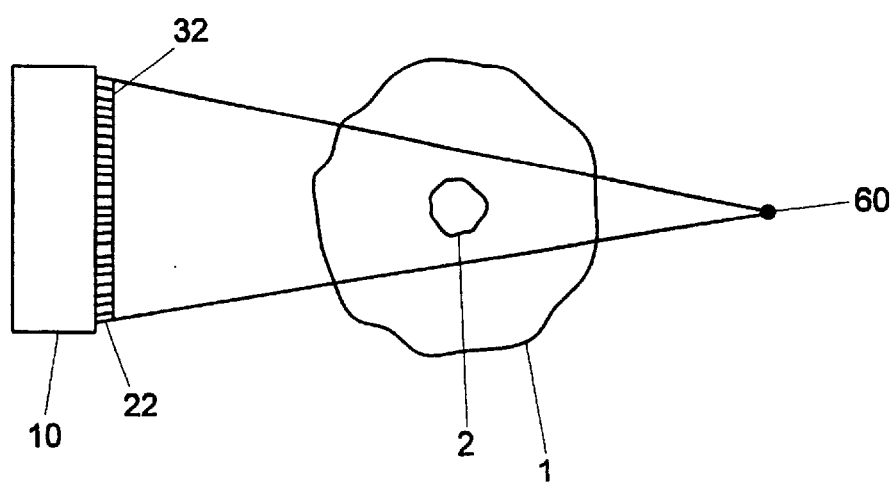
FIG. 2B is a schematic top plan view of the arrangement shown in FIG. 2A.

An improvement in this regard is provided by the arrangement shown in FIG. 2. There the parallel collimator 21 has been replaced with a focused collimator 22, and the planar radiation source 50 has been replaced with a line source 60. In the focused collimator 22 the passages 32 are directed towards a single focus line 33, which substantially coincides with the line-shaped radiation source 60. More particularly, each centerline of a passage 32 intersects the line-shaped radiation source 60 at an angle of substantially 90°. Such a collimator is also referred to as fan beam collimator. Alternatively, the passages of the collimator can be directed in two mutually perpendicular directions towards two different focus lines (astigmatic collimator), as is known per se, in which case the line-shaped radiation source 60 is positioned along one of those focus lines.

The use of a line source 60 together with a fan beam collimator 22 provides an advantage over the combination of a planar source 50 and a parallel collimator 21 in that the radiation produced is better utilized, and hence the amount of radioactive matter of the radiation source can be less. Further, the emission recording is improved because converging collimators count more photons than do parallel collimators. Furthermore, converging collimators, in comparison with parallel collimators, provide the advantage that a "point" illuminates several pixels, which can be designated as a magnifying effect, so that a greater definition is obtained both in the projection image and in the tomography image.

Figure 3A:
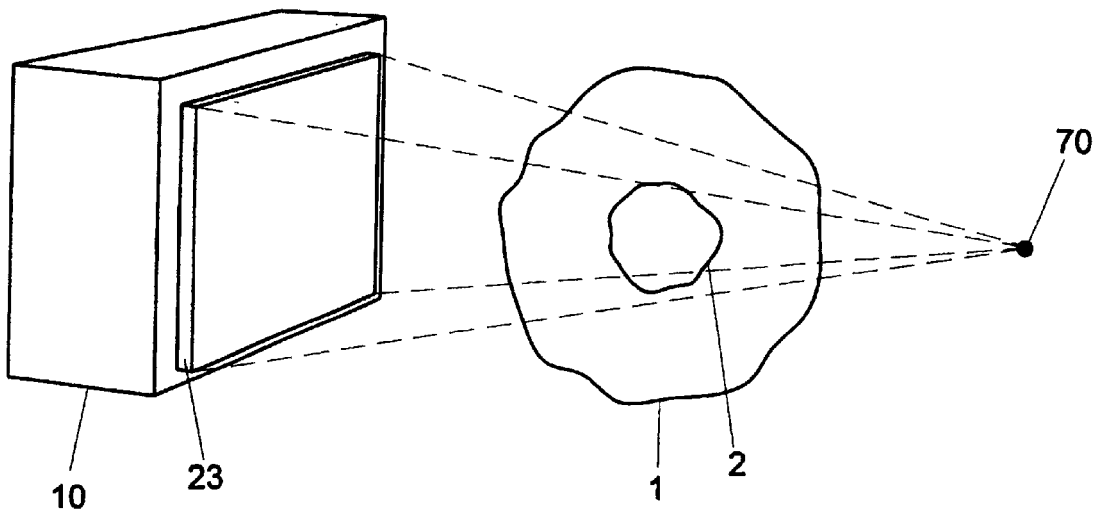
FIG. 3A is a schematic perspective view of a known arrangement for making combined emission/transmission recordings, with a cone beam collimator and a fixed point source.
Figure 3B:
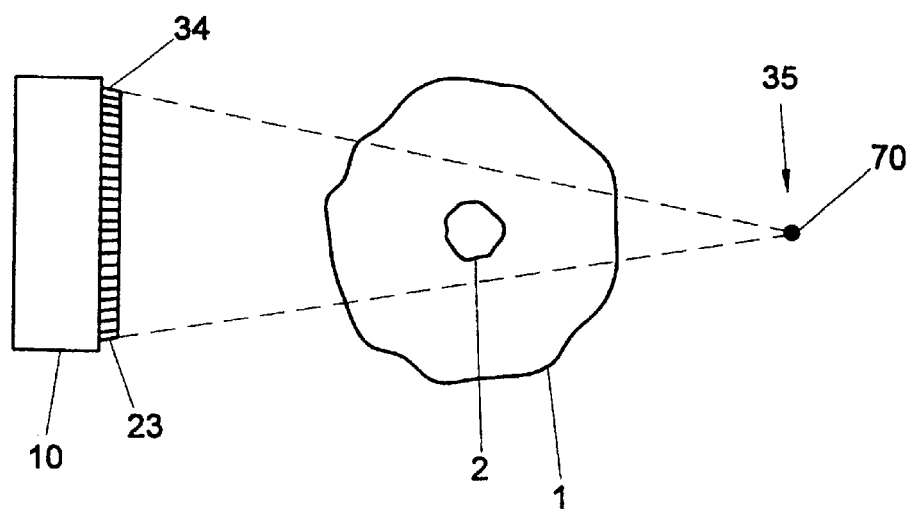
FIG. 3B is a schematic top plan view of the arrangement shown in FIG. 3A.

Another improvement in this regard is provided by the arrangement shown in FIG. 3. There the parallel collimator 21 has been replaced with a focused collimator 23, and the planar radiation source 50 has been replaced with a point source 70. In the focused collimator 23 the passages 34 are directed towards a single focus point 35, which coincides substantially with the point-shaped radiation source 70. Such a collimator is also referred to as a cone beam collimator. In the combination of a cone beam collimator 23 and a point source 70, the radiation energy of the source is used even more efficiently than in a fan beam collimator.

Thus a converging collimator makes it possible to use a compact (line or point) source, so that the amount of radioactivity that is needed for making a recording can be limited. Further, it can be stated in general that images made with a converging collimator have much better definition and noise properties than do images made with a parallel collimator.

A problem playing a role in producing a combined emission/transmission recording is that photons coming from the external source may end up in the emission image, and that photons emitted by the object itself may end up in the transmission image. Such incorrectly interpreted photons signify a reduction of the accuracy or quality of the images obtained (image degradation).

In the publication "A scanning Line Source for Simultaneous Emission and Transmission Measurements in SPECT" by P. Tan et al in The Journal of Nuclear Medicine, vol. 34, no. 10, October 1993, p. 1752, an arrangement is described which enables obtaining a separation between the emission-derived radiation and the transmission-derived radiation. That known arrangement is schematically represented in FIG. 4. There the collimator 24 is a parallel collimator, which entails the above-described disadvantages, compared with converging collimators. The radiation source 80 in FIG. 4 is a line-shaped radiation source, which is provided with a shielding 81 to ensure that the radiation 82 that leaves the line source 80 and strikes the camera 10 is located in a single plane 83 which includes the line source 80.

The line source 80, whose longitudinal direction is directed parallel to the front face of the collimator 24, is so directed that the plane 83 is perpendicular to the collimator 24. Thus, during the making of a recording the collimator is illuminated according to a line-shaped irradiation pattern 25 (line-shaped "light spot") (projection of the radiation beam on the camera), which is defined by the line of intersection of the plane 83 and the front face of the collimator 24. The radiation 82 that strikes the collimator 24 at right angles is allowed to pass by the passages 36 in the collimator 24 and reaches the camera 10. Thus a line-shaped area of the camera 10 is irradiated with transmission photons. Photons that strike the camera 10 outside this line-shaped area are emission photons.

The line source 80 which, as already mentioned hereinabove, is mounted in a subframe (not shown), is moved relative to the subframe, and hence relative to the camera 10, in a direction parallel to the front face of the collimator 24, perpendicular to its longitudinal direction, as indicated by the arrow P. Thus the line-shaped irradiation pattern 25 of the camera 10 is moved in a direction perpendicular to the longitudinal direction of that line-shaped area 25, to scan the surface of the camera 10. As schematically illustrated in FIG. 4B, a control element 84 is present, which receives information regarding the position of the line source 80 and calculates therefrom what detection elements (pixels) of the camera 10 receive transmission radiation; the image signals of those pixels are added to an image memory 85 for the transmission image, while the image signals of the other pixels are added to an image memory 86 for the emission image. Thus, as it were, with respect to the pixels of the camera 10 a moving transmission window 87 is defined, which window 87 defines the pixels that contribute to the transmission image, and hence corresponds to the moving irradiation pattern 25. The above-discussed technique will therefore be referred to hereinafter, for short, as "moving transmission window".

Although this known method as such is capable of rendering the emission image less sensitive to transmission photons, there is yet an important inherent disadvantage, associated with the use of a parallel collimator. In fact, it is found in practice that the number of photons that, starting from the line source 80, reaches the pixels of the camera 10 as defined by the transmission window 87 is particularly small. The result is that the transmission image is of low light intensity, unsharp and contains much noise, while being particularly sensitive to photons coming from the object 1 itself (which really belong in the emission image.)

The present invention proposes a construction which does not have the disadvantages mentioned, at least does so to a much lesser extent, and combines the advantages mentioned.

A first embodiment 100 of the apparatus according to the present invention is illustrated in FIG. 5. What this apparatus 100 has in common with the known devices is that a camera 10, a collimator 120 and a radiation source 150 are present, with the camera 10 and the collimator 120 on the one hand and the radiation source 150 on the other being arranged on opposite sides of an object 1. In this embodiment 100 the collimator 120 is a converging collimator with at least one focal line or convergence line 121. Preferably, the collimator 120 is a fan beam collimator. The radiation source 150 is a substantially line-shaped source, which is arranged adjacent the focal line 121 and preferably coincides with the focal line 121. The line source 150 is provided with radiation-directing means 151 which ensure that the radiation 152 is emitted only in a plane 153 which contains the line source 150; these radiation-directing means 151 can be equal to the means 81 discussed in the publication mentioned. In the figure, the radiation-directing means 151 are illustrated as a shield 155 extending around the line source 150, which shield 155 can be a cylindrical shield whose cylinder axis coincides with the focal line 121 of the fan beam collimator 120. The shield 155 is provided with an elongate passage slit 156 parallel to the line source 150, which elongate passage slit 156 defines the direction in which radiation 152 coming from the line source 150 is allowed to pass through the shield 155. Preferably, the shield 155 comprises a radiation-absorbing material.

Thus, for the purpose of the transmission image, the camera 10 is illuminated with an elongate irradiation pattern 125, which is defined by the line of intersection of the plane 153 and the camera 10. According to an important aspect of the present invention, means are provided for moving the elongate irradiation pattern 125, perpendicularly to the longitudinal direction of the irradiation pattern 125, in such a manner that the transmission radiation 152 always comes from the direction of the focal line 121 of the collimator 120.

Figure 5A:
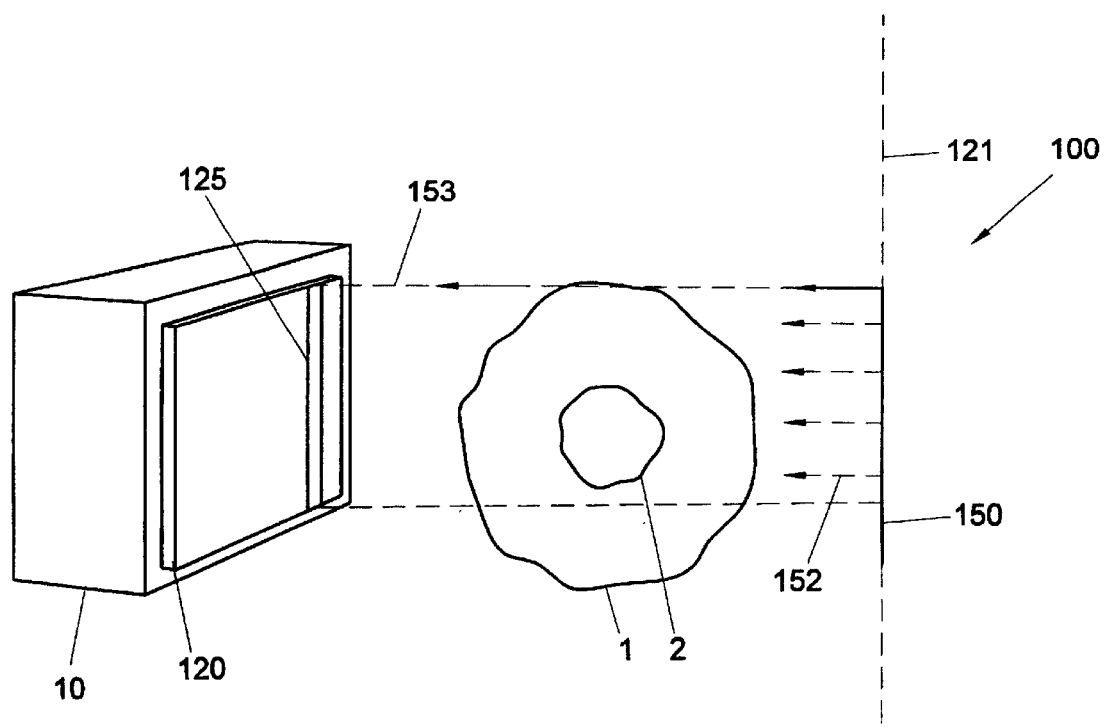
FIG. 5A is a schematic perspective view of a first embodiment of the apparatus according to the present invention for making combined emission/transmission recordings, with a fan beam collimator and a rotary line source.
Figure 5B:
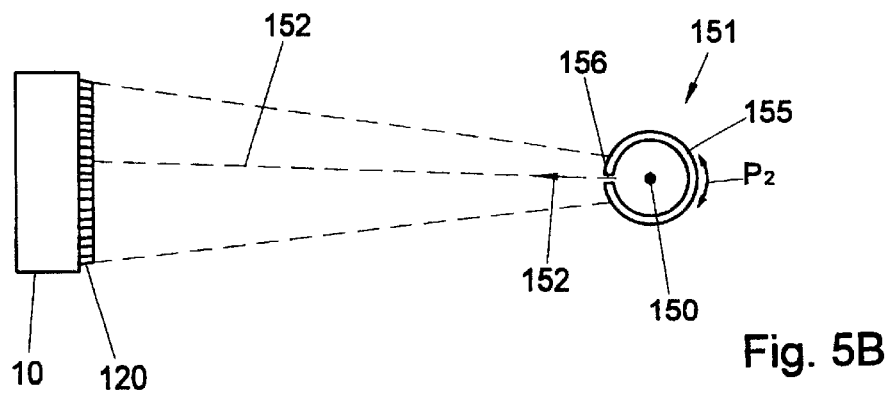
FIG. 5B is a schematic top plan view of the arrangement shown in FIG. 5A.

Within the scope of the concept of the invention, this can be effected in different ways. FIG. 5B illustrates a first variant. There the line source 150 is fixedly positioned at the focal line 121 of the collimator 120, and the slit 156 of the shield 155 is movable in a direction perpendicular to the longitudinal direction thereof. In the embodiment shown, the shield 155 is arranged for rotation relative to the focal line 121 of the collimator 120, as indicated by the arrow P2. It is also possible, however, that the shielding comprises a screen plate, arranged between the line source and the collimator, with a passage slit provided therein, which screen plate is linearly moveable.

Since the manner in which the rotatable arrangement of the shield 155 is accomplished is of no importance for a good understanding of the present invention, and those skilled in the art will be able without any problems to design such a rotatable arrangement, that arrangement will not be further discussed here.

Figure 5C:
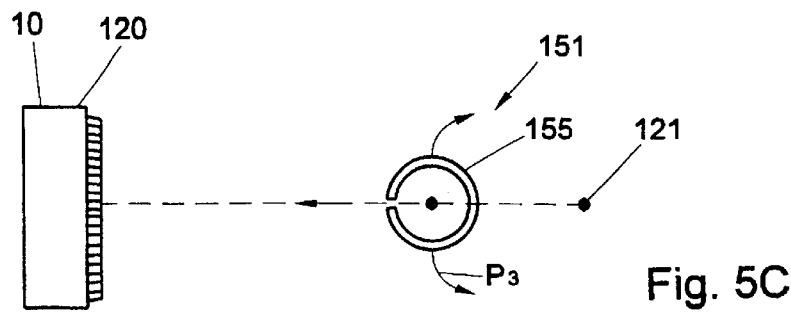
FIG. 5C is a top plan view similar to FIG. 5B, of a variant of the apparatus shown in FIG. 5A.

FIG. 5C illustrates a second variant. There the combination of the line source 150 and the shield 155 is in a position removed from the focal line 121, in the example shown between the focal line 121 and the camera 10. The line source 150, the passage slit 156 in the shield 155, and the focal line 121 are disposed in one plane 153. The combination of the line source 150 and the shield 155 is mounted in the subframe (not shown), in such a manner that the combination is rotatable relative to the focal line 121, as indicated by the arrow P3, so that the plane 153 performs a swinging motion relative to the focal line 121.

A second embodiment 200 of the apparatus according to the present invention is illustrated in FIG. 6. What this apparatus 200 has in common with the above-discussed apparatus 100 of the first embodiment is that a camera 10, a collimator 220 and a radiation source 250 are present, with the camera 10 and the collimator 220 on the one hand and the radiation source 250 on the other being arranged on opposite sides of an object 1, and that the collimator 220 is a converging collimator with at least one focal line or convergence line 221, preferably a fan beam collimator. In this embodiment 200 the radiation source 250 is a substantially point-shaped source, which is arranged adjacent or in that focal line 221. The point source 250 is provided with radiation-directing means 251 which ensure that the radiation 252 is emitted only in a plane 253 which is perpendicular to the focal line 221. In the figure, the radiation-directing means 251 are illustrated as a shield 255 extending around the point source 250, which shield 255 can be a spherical shield whose center lies on the focal line 221 of the fan beam collimator 220. The shield 255 comprises an elongate passage slit 256 perpendicular to the focal line 221, which elongate slit 256 defines the direction in which radiation 252 coming from the point source 250 is allowed to pass by the shield 255. Preferably, the shield 255 comprises a radiation-absorbing material.

Accordingly, as in the first embodiment 100, in the second embodiment the camera 10, for the purpose of the transmission image, is illuminated with an elongate irradiation pattern 225, which is defined by the line of intersection of the plane 253 and the camera 10. According to an important aspect of the present invention, means are provided for displacing the elongate irradiation pattern 225, perpendicularly to the longitudinal direction of the irradiation pattern 225, in such a manner that the transmission radiation always comes from the direction of the focal line 221 of the collimator 220. In the illustrated embodiment, this is accomplished in that the combination of the point source 250 and the shield 255 is mounted in the subframe (not shown), in such a manner that the combination is movable along the focal line 221, as indicated by the arrow P4.

Since the manner in which this movable arrangement is accomplished is no importance for a good understanding of the present invention, and those skilled in the art will be able without any problems to design such a movable arrangement, that arrangement will not be further discussed here.

An important advantage of this second embodiment 200 over the first embodiment 100 is that a point source can be used, so that the amount of radioactive material that is needed for making a recording can be reduced considerably, while the local intensity can be high, so that a transmission image is only to a slight extent affected by emission radiation.

It is noted that in the example discussed the illumination pattern is a line-shaped pattern, but that the pattern being line-shaped, though preferable, is not essential to the present invention. In principle, the illumination pattern may have an arbitrary shape, as long as that shape is known beforehand, in order that the control device "knows", at any rate can compute, what pixels of the detector at any given time contribute to the transmission image.

Figure 7A:
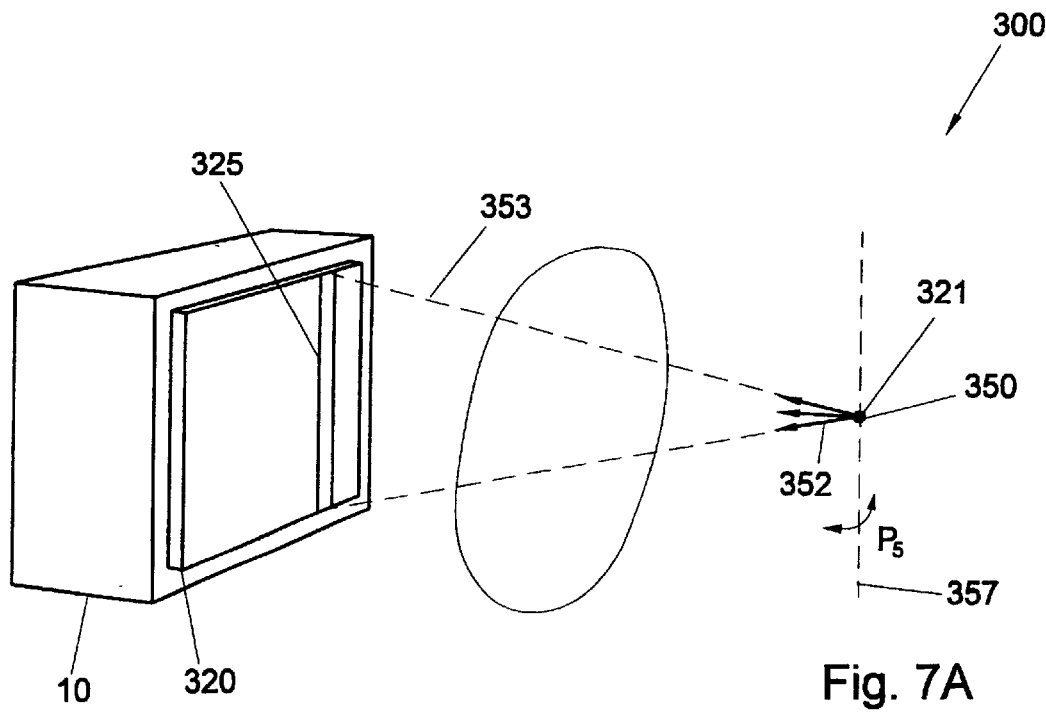
FIG. 7A is a schematic perspective view of a third embodiment of the apparatus according to the present invention for making combined emission/transmission recordings, with a cone beam collimator and a rotary point source.
Figure 7B:
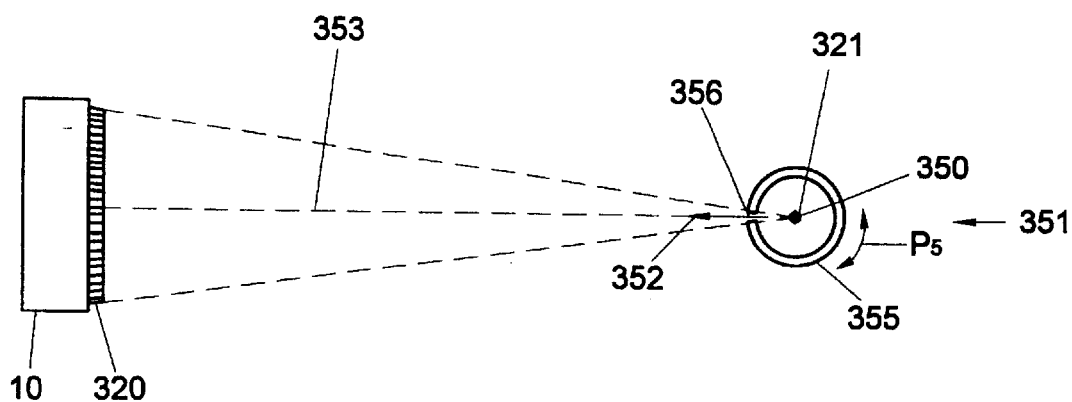
FIG. 7B is a schematic top plan view of the apparatus shown in FIG. 7A.

A third embodiment 300 of the apparatus according to the present invention is illustrated in FIG. 7. What this apparatus 300 has in common with the above-described apparatus 200 of the second embodiment is that a camera 10, a collimator 320 and a radiation source 350 are present, with the camera 10 and the collimator 320 on the one hand and the radiation source 350 on the other being arranged on opposite sides of an object 1; that the collimator 320 is a converging collimator; and that the radiation source 350 is a substantially point-shaped source. In this embodiment 300 the collimator 320 is a converging collimator with a single convergence point 321 (cone beam collimator). The radiation source 350 is arranged adjacent that convergence point 321 and is preferably disposed in that convergence point 321. The point source 350 is provided with radiation-directing means 351 which ensure that the radiation 352 is only emitted in a plane 353 which contains the convergence point 321. In the figure, these radiation-directing means 351 are illustrated as a shield 355 extending around the point source 350, which shield 355 can be a spherical shield whose center coincides with the convergence point 321 of the cone beam collimator 320. The shield 355 is provided with an elongate passage slit 356, which defines the direction in which radiation 352 coming from the point source 350 is allowed to pass by the shield 355. Preferably, the shield 355 comprises a radiation-absorbing material.

Accordingly, as in the first embodiment 100 and the second embodiment 200, in the third embodiment 300, the camera 10, for the purpose of the transmission image, is illuminated with an elongate irradiation pattern 325, which is defined by the line of intersection of the plane 353 and the camera 10. According to an important aspect of the present invention, means are provided for moving the elongate irradiation pattern 325, perpendicularly to the longitudinal direction of the irradiation pattern 325, in such a manner that the transmission radiation 352 always comes from the direction of the convergence point 321 of the collimator 320. In the illustrated embodiment, this is accomplished in that the combination of the point source 350 and the shield 355 is mounted in the subframe (not shown), in such a manner that the shield 355 is rotatable relative to an axis of rotation 357 which intersects the convergence point 321 of the cone beam collimator 320 and which lies in the plane 353, as indicated by the arrow P5. Since the manner in which this rotatable arrangement is accomplished is of no importance for a good understanding of the present invention, and those skilled in the art will be able without any problems to design such a rotatable arrangement, that arrangement will not be further discussed here.

As in the first embodiment 100, it is possible in the third embodiment 300 too, that the shielding comprises a screen plate, arranged between the point source and the collimator, with a passage slit provided therein, which screen plate is linearly movable in a direction perpendicular to the longitudinal direction of the passage slit. Further, with reference to FIG. 5C, it is noted that in this third embodiment 300 too, it is not necessary that the point source 350 coincides with the convergence point 321 of the collimator 320.

Accordingly, all three of the embodiments discussed involve, in accordance with the present invention, a planar radiation beam which illuminates the camera 10 according to an elongate illumination pattern 125; 225; 325, and that elongate illumination pattern is moved over the camera 10. In a similar manner to that described in the article by P. Tan et al (see FIG. 4) mentioned earlier, a transmission window moving along with that elongate illumination pattern can be defined in that a control element (not shown for the sake of simplicity) calculates from, respectively, the orientation (FIGS. 5 and 7) and position (FIG. 6) of the radiation source what pixels of the camera contribute to the transmission image. Since this is known per se, this will not be further explained here.

Figure 8:
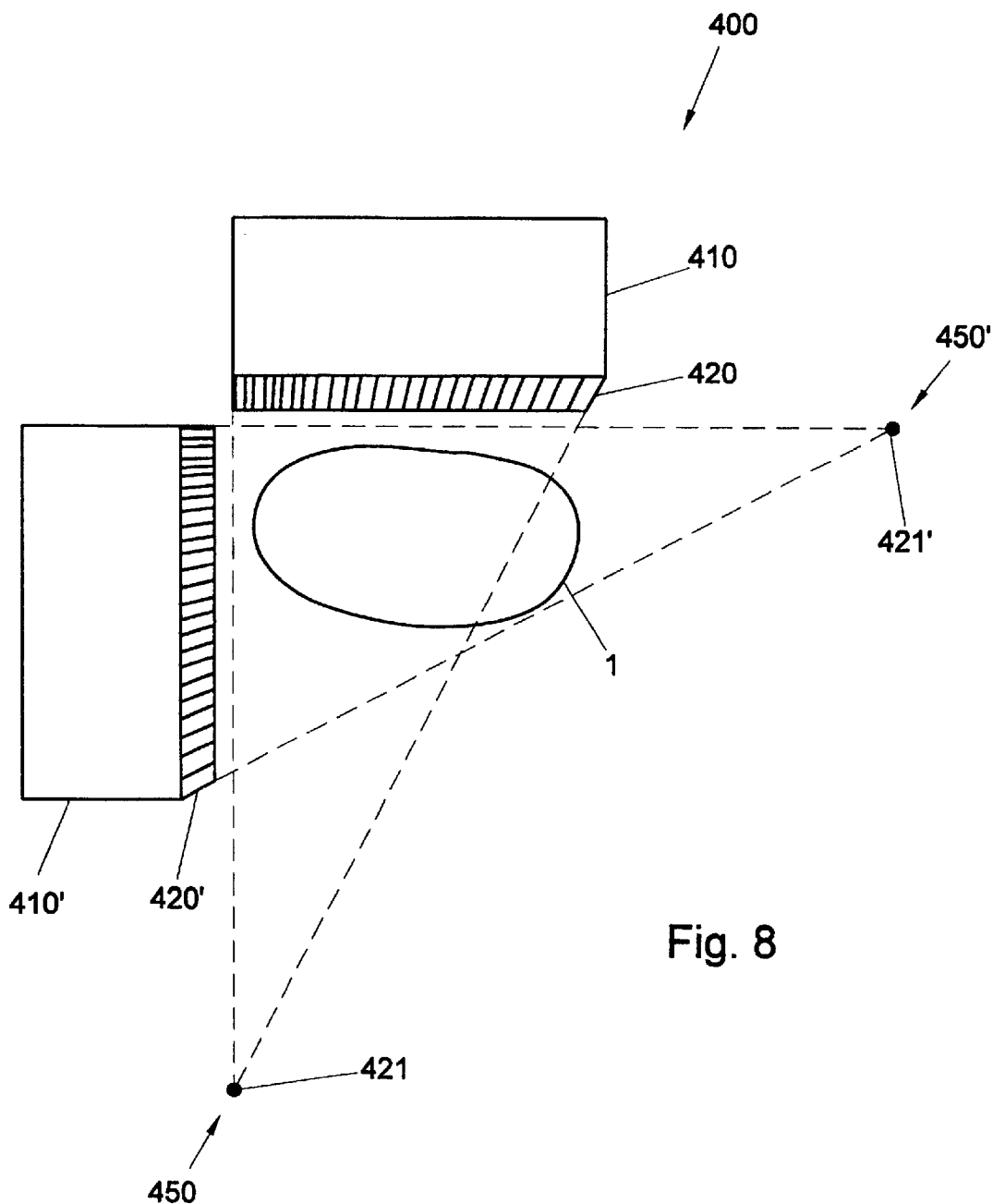
FIG. 8 is a schematic side elevation of a fourth embodiment of the apparatus according to the present invention for making combined emission/transmission recordings, with two fan beam collimators and two moving point sources.

FIG. 8 illustrates a side elevation of a fourth embodiment of the apparatus according to the present invention, in which a further improvement is embodied. This fourth embodiment 400 comprises two cameras 410 and 410', which are arranged at an angle relative to each other; in the example shown, the two cameras 410 and 410' are at right angles to each other. Each camera 410, 410' is provided with a fan beam collimator 420, 420', respectively. Each fan beam collimator 420, 420' has a focal line 421, 421', respectively, which is perpendicular to the plane of the paper. Arranged at each focal line 421, 421' is a point source 450, 450', respectively, which is movable substantially along the corresponding focal line 421, 421'. The operation of the combination of the camera 410, the collimator 420 and the movable point source 450 is similar to the operation of the combination of the camera 10, the collimator 220 and the movable point source 250 as described with reference to FIGS. 6A and 6B; likewise, the operation of the combination of the camera 410', the collimator 420' and the movable point source 450' is similar to the operation of the combination of the camera 10, the collimator 220 and the movable point source 250 as described with reference to FIGS. 6A and 6B.

According to an important aspect of this fourth embodiment 400 the position of the focal line 421, 421', respectively, is not symmetrical with respect to the corresponding collimator 420 and 420', respectively. As is clearly illustrated in FIG. 8, the focal line 421 of the one collimator 420 has been moved in the direction of the other collimator 420', and the focal line 421' of the other collimator 420' has been moved in the direction of the one collimator 420.

In the example shown, each focal line 421 and 421', respectively, lies in a plane perpendicular to an edge of the corresponding collimator 420 and 420', respectively, so that each collimator 420 and 420', respectively, can be designated as a "half" fan beam collimator.

An advantage of the fourth embodiment 400 is that it obviates situations where, if a portion of the object 1 is located close to a camera, that portion is not imaged at all ("truncated").

FIGS. 9A and 9B illustrate two mutually perpendicular side elevations of a fifth embodiment according to the present invention, in which a further improvement is embodied. This fifth embodiment 500 comprises two cameras 510 and 510', which are arranged at an angle relative to each other; in the example shown, the two cameras 510 and 510' are at right angles to each other. Each camera 510, 510' is provided with a cone beam collimator 520 and 520', respectively. Each cone beam collimator 520, 520' has a convergence point 521, 521', respectively. Arranged adjacent each convergence point 521, 521', respectively, is a point source 550, 550', respectively, which is rotatable about an axis perpendicular to the plane of the paper of FIG. 9A. The operation of the combination of the camera 510, the collimator 520 and rotatable point source 550 is similar to the operation of the combination of the camera 10, the collimator 320 and rotatable point source 350 as described with reference to FIGS. 7A and 7B; likewise, the operation of the combination of the camera 510', the collimator 520' and rotatable point source 550' is similar to the operation of the combination of the camera 10, the collimator 320 and rotatable point source 350 as described with reference to FIGS. 7A and 7B.

According to an important aspect of this fifth embodiment 500 the position of the convergence point 521, 521' is not symmetrical with respect to the corresponding collimator 520, 520'. As is clearly illustrated in FIGS. 9A and 9B, the convergence point 521 of the one collimator 520 has been moved in the direction of the other collimator 520', and the convergence point 521' of the other collimator 520' has been moved in the direction of the one collimator 520.

In the example shown, each convergence point 521, 521' lies on a line perpendicular to a corner point of the corresponding collimator 520, 520', so that each collimator 520, 520' can be designated as a "quarter" cone beam collimator.

The use of cone beam collimators has utility in particular in imaging smaller organs or parts of the body, such as for instance brains. For obtaining a sharper image it is desirable that the distance between the object and the camera be made as small as possible. With two cameras at right angles to each other, a half cone beam is not adequate to optimally image the head of a patient, because the distance between the head and one of the cameras must then increase and therefore entails unsharpness. The fifth embodiment 500 solves this problem. The object can be placed closer to the cameras, while avoiding that a portion of the object 1 that is located close to a camera is not imaged at all ("truncated").

In FIGS. 9A and 9B a possible axis of rotation for the cameras 510, 510', respectively, is designated by the reference numeral 599.

Asymmetries other than an exact quarter-cone can also be used, for instance at other angles between the cameras.

FIG. 10 illustrates a further improvement, proposed by the present invention, for increasing the definition of the image in transmission tomography. This definition is to an important extent determined by the size of the source used. In practice, it is difficult to reduce the size of the source while yet retaining a good radiation strength of the source: this would mean inter alia that the source would have to be very concentrated. According to the present invention, effectively a very small source size is achieved (virtual point source 650) by arranging a source 651 with spatial dimensions behind a strongly absorbing screen plate 652, in which a preferably conical hole 653 is formed, the size of the hole 653 corresponding to the desired size of the source. This further provides the advantage that it is possible to regulate the strength of the radiation in a direction-dependent manner; this results in a certain intensity profile that can be determined through the choice of the source shape.

In FIG. 10 it is further illustrated that a moving radiation beam can be provided by moving a screen plate 655 with a slit 656 of a desired shape in front of the virtual point source 650.

A camera 610 receives radiation solely from the direction defined by the hole 653 and the slit 656, which direction is indicated in FIG. 10 by a dotted line 660. The amount of radiation in this direction corresponds substantially to the length L of the three-dimensional source 651 proper, measured along this dotted line 660. It will be clear that it is possible so to choose the three-dimensional shape of the three-dimensional source 651, through the addition/removal of radioactive material at the back of the three-dimensional source 651, that the desired radiation profile is achieved.

The beam width and emission strength can be regulated inter alia by the magnitude of the hole 653 in the absorbing plate 652, the shape of the source 651, and the mutual distances between the source, the absorbing plate 652 and the moving screen plate 655. The obliqueness of the conical hole 653 at the front of the highly absorbent plate 652 partly determines what portion of the camera 610 is still irradiated.

It will be clear to those skilled in the art that the scope of protection of the present invention as defined by the claims is not limited to the embodiments discussed and represented in the drawings, but that it is possible to change or modify the represented embodiments of the tomography device according to the invention within the scope of the concept of the invention.

Thus, it is possible, for instance, to determine in a different way what pixels furnish transmission image signals. In general, the energy of the transmission photons is different from the energy of the emission photons (for instance, 100 keV and 140 keV, respectively); it is therefore possible for the detected photons to be selected according to energy.

Further, it is noted that in nuclear medicine normally the combination of an emission recording with a transmission recording is desired. However, the present invention is also applicable in situations where only a transmission recording is desired.

Figure 11A:
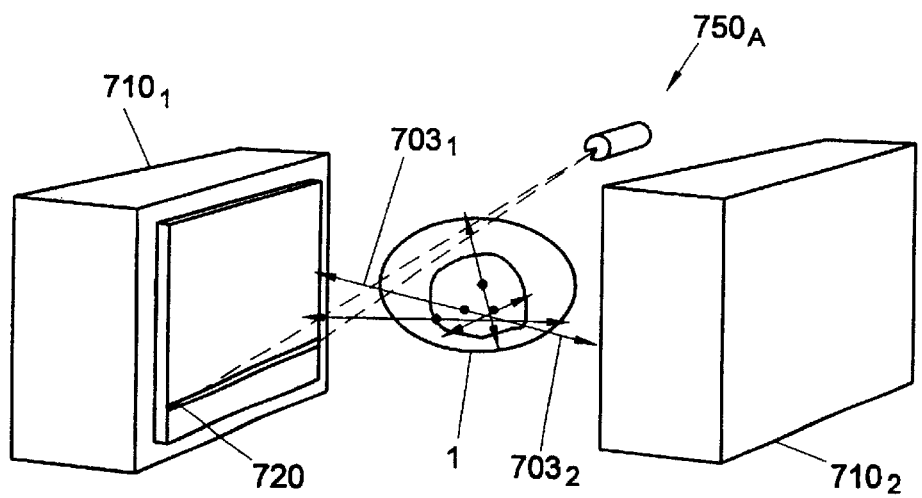
FIGS. 11A–C illustrate schematically a possible variant of the present invention in the case of PET.
Figure 11B:
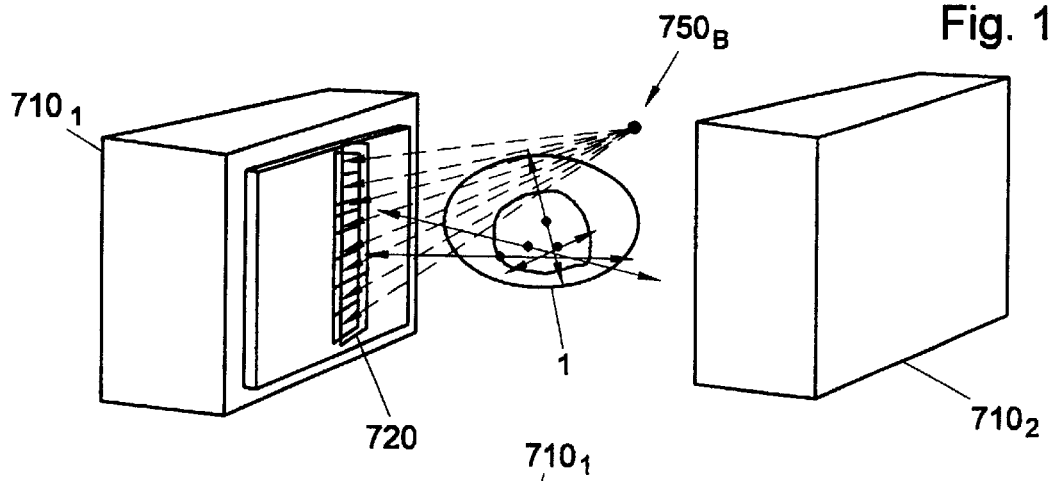
Figure 11C:
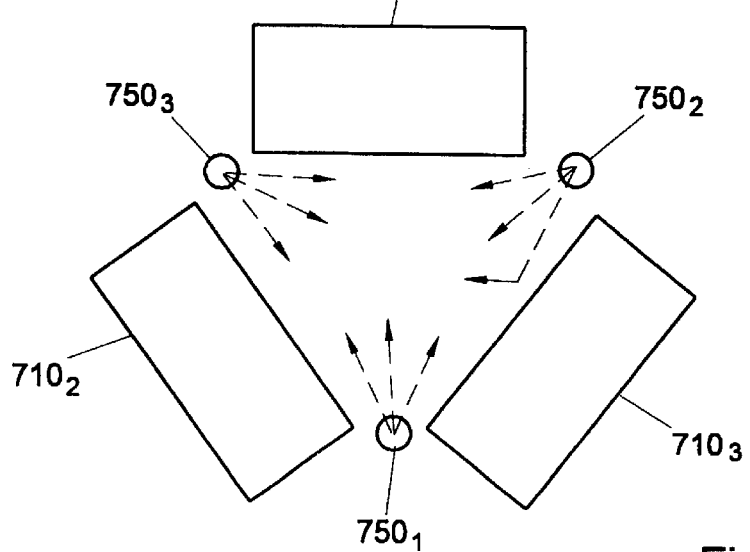

The present invention is also applicable in PET systems (Positron Emission Tomography). In these systems, a radioactive substance is injected into the patient, which substance radiates positrons. The emitted positrons annihilate with electrons present in the body of the patient. The distance traveled by a positron in the body before it annihilates is generally only a few millimeters. Upon annihilation two gamma quants are released, each of 511 keV, which quants move in exactly opposite directions. As illustrated in FIG. 11, these two quants $703_1$ and $703_2$ are detected with two oppositely arranged position-sensitive detectors $710_1$, $710_2$. The signals of these detectors are assessed for coincidence in a processing circuit: when from the two detectors two signals arise simultaneously, it is assumed that these signals "belong together", that is, are caused by quants released upon the same annihilation. The two positions where those two quants strike the two detectors define a line on which the annihilation must have taken place. Because this line is fixed through the coincidence of the two detections, no collimator is needed in a PET system. A consequence of this is that PET is much more sensitive than SPECT. Further, PET is sometimes operated with a SPECT system with two detectors without collimators (see FIGS. 11A and 11B). It is also possible to use several detectors $710_1$, $710_2$, $710_3$ (see FIG. 11C).

PET too can be combined with transmission sources 750 as described in the foregoing with regard to SPECT. In that case, too, it is desired to perform a correction for attenuation. As has been described in the foregoing, for this purpose use can be made of a linearly movable point source on the convergence line of a fan beam collimator, or a rotary point source adjacent the convergence point of a cone beam collimator.

In the case of a PET system, however, it is important that at the location of the moving irradiation pattern a collimator is arranged before the camera, while no collimator is arranged before the positions of the camera that are located next to the irradiation pattern. What is thus accomplished is that at the location of the transmission window unnecessary emission radiation is blocked.

Figure 6A:
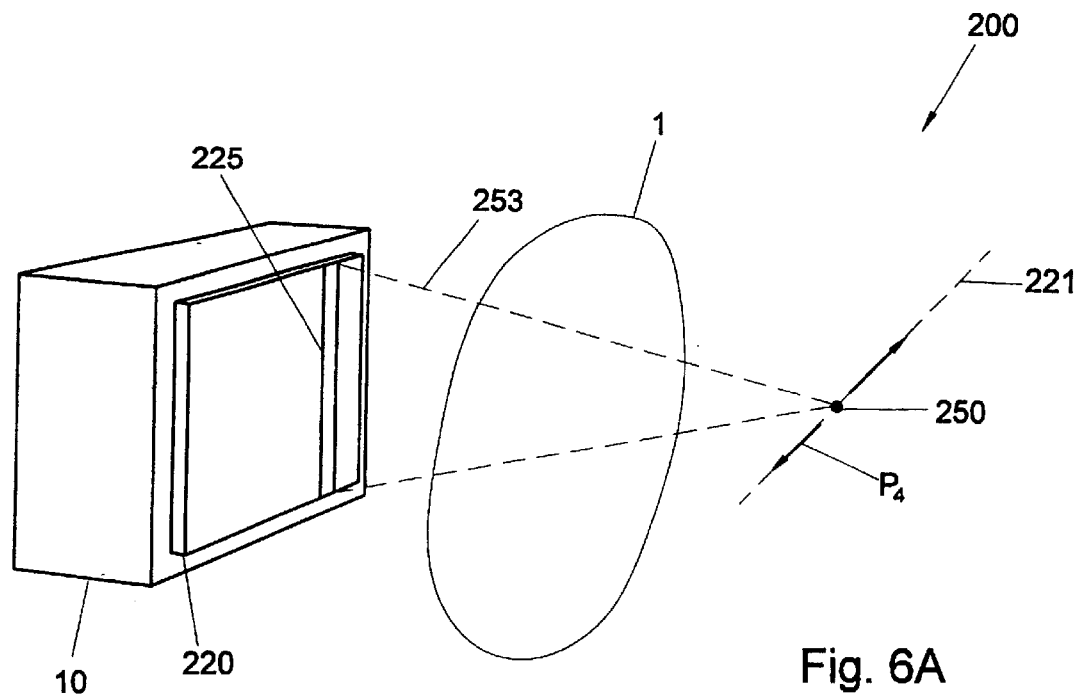
FIG. 6A is a schematic perspective view of a second embodiment of the apparatus according to the present invention for making combined emission/transmission recordings, with a fan beam collimator and a moving point source.
Figure 6B:
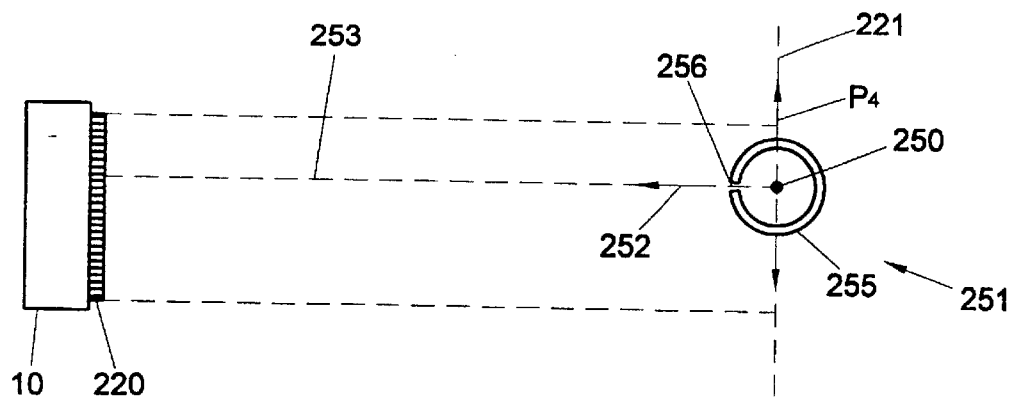
FIG. 6B is a schematic top plan view of the apparatus shown in FIG. 6A.

According to a particular aspect of the present invention, for that purpose use can be made of a line-shaped collimator element 720, whose construction and operation are substantially the same as those of the above-discussed collimator arranged stationarily in front of the entire detection surface of the camera, with the understanding that the collimator element 720 has a strip-shaped appearance, that is, a length dimension substantially corresponding to the dimension of the detection surface of the camera and a width substantially corresponding to the width of the irradiation pattern. The collimator element 720 is movably arranged, and is moved perpendicularly to its longitudinal direction in conjunction with the displacement of the irradiation pattern. In the case wherein the moving irradiation pattern is generated by a linearly moving point source $750_A$ (see FIG. 11B; FIGS. 6A–B), it suffices to move the collimator element 720 linearly. In the case where the moving irradiation pattern is generated by a rotary line source $750_B$ (see FIG. 11A; FIGS. 5A–C), the longitudinal direction of the collimator element is parallel to its convergence line, and the collimator element 720 should further be rotated in such a manner that its convergence line remains substantially stationary.

Summarizing, the present invention provides a device for obtaining tomography images, which on the one hand provides a very good separation between transmission images and emission images and on the other hand provides an improved image strength (counts per pixel) in the transmission image, so that the images provided have an improved signal-to-noise ratio over the prior art.

What is claimed is:

1. An apparatus for making combined transmission and emission recordings of an object using radiation, the apparatus comprising:

a radiation source;

a camera sensitive to radiation from the radiation source and to emitted radiation from the object, the radiation and the emitted radiation having different energy levels;

a collimator arranged between the radiation source and the camera;

radiation-directing means which ensure that the radiation of the radiation source is radiated in a planar radiation beam so that the camera is illuminated according to a substantially line-shaped irradiation pattern;

and means for moving the line-shaped irradiation pattern over the camera in a direction substantially perpendicular to the longitudinal direction thereof;

wherein the collimator is fixed relative to the camera; and wherein the collimator is a focused fan beam collimator.

2. The apparatus according to claim 1, wherein the collimator has at least one convergence line;

wherein the radiation source is a line-shaped radiation source, whose longitudinal direction is directed parallel to the convergence line of the collimator;

wherein said plane in which the radiation is radiated contains the convergence line of the collimator; and wherein the collimator is a focused cone beam collimator.

3. The apparatus according to claim 2, wherein the radiation-directing means comprises a shielding, which is provided with a movable passage slit.

4. The apparatus according to claim 2, wherein the line-shaped radiation source substantially coincides with the convergence line of the collimator;

wherein the shielding extends around the radiation source; and wherein the shielding is rotatable with regard to the convergence line of the collimator.

5. The apparatus according to claim 2, wherein the line-shaped radiation source is spaced from the convergence line of the collimator;

wherein the shielding extends around the radiation source; and wherein the combination of the radiation source and the shielding is rotatable with respect to the convergence line of the collimator.

6. The apparatus according to claim 1, wherein the collimator has at least one convergence line;

wherein the radiation source is a point-shaped radiation source, which is arranged adjacent the convergence line of the collimator;

wherein said plane in which the radiation is radiated is substantially perpendicular to the convergence line of the collimator; and wherein means are present for moving said plane in a direction parallel to the convergence line of the collimator.

7. The apparatus according to claim 6, wherein the radiation-directing means comprises a shielding which is provided with a movable passage slit.

8. The apparatus according to claim 7, wherein the point-shaped radiation source lies substantially on the convergence line of the collimator;

wherein the shielding extends around the radiation source; and wherein the combination of the radiation source and the shielding is movable along the convergence line of the collimator.

9. The apparatus according to claim 1, wherein a first camera and a second camera are arranged at an angle with respect to each other, which angle is about 90°;

wherein the first camera is provided with a first fan beam collimator, whose focal line is located on the side of the first fan beam collimator directed to the second camera;

wherein the second camera is provided with a second fan beam collimator, whose focal line is located on the side of the second fan beam collimator directed to the first camera;

wherein the focal line of the first fan beam collimator and the focal line of the second fan beam collimator are mutually parallel; and wherein a first point source is movable along the focal line of the first fan beam collimator and wherein a second point source is movable along the focal line of the second fan beam collimator.

10. The apparatus according to claim 1, wherein a first camera and a second camera are arranged at an angle with respect to each other, which angle is about 90°;

wherein the first camera is provided with a first cone beam collimator, whose focal point is located on the side of the first cone beam collimator directed to the second camera;

wherein the second camera is provided with a second cone beam collimator, whose focal point is located on the side of the second cone beam collimator directed to the first camera;

wherein adjacent the focal point of the first cone beam collimator a first point source is arranged, which is associated with a first shielding element with a first movable passage slit; and wherein adjacent the focal point of the second cone beam collimator a second point source is arranged, which is associated with a second shielding element with a second movable passage slit;

wherein the first passage slit and the second passage slit are mutually parallel; and wherein the first passage slit is movable in a direction perpendicular to the first passage slit, and wherein the second passage slit is movable in a direction perpendicular to the second passage slit.

11. The apparatus according to claim 1, the apparatus further comprising:

a control device for computing whether sensed radiation is emitted radiation or source radiation.

12. An apparatus for making transmission and/or emission recordings of an object using radiation, the apparatus comprising:

a radiation source;

a camera sensitive to radiation from the radiation source and to emitted radiation from the object, the radiation and the emitted radiation having different energy levels;

a collimator arranged between the radiation source and the camera;

radiation-directing means which ensure that the radiation of the radiation source is radiated in a planar radiation beam so that the camera is illuminated according to a substantially line-shaped irradiation pattern; and means for moving the line-shaped irradiation pattern over the camera in a direction substantially perpendicular to the longitudinal direction thereof;

wherein the collimator is fixed relative to the camera; and wherein the collimator is a focused fan beam collimator.

13. The apparatus according to claim 12, the apparatus further comprising:

a control device for computing whether sensed radiation is emitted radiation or source radiation according to energy level.

14. An apparatus for making combined transmission and emission recordings of an object using radiation, the apparatus comprising:

a radiation source;

a camera sensitive to radiation from the radiation source and to emitted radiation from the object, the radiation and the emitted radiation having different energy levels;

a collimator arranged between the radiation source and the camera;

radiation-directing means which ensure that the radiation of the radiation source is radiated in a planar radiation beam so that the camera is illuminated according to a substantially line-shaped irradiation pattern; and means for moving the line-shaped irradiation pattern over the camera in a direction substantially perpendicular to the longitudinal direction thereof;

wherein the collimator is fixed relative to the camera; and wherein the collimator is a focused cone beam collimator.

15. The apparatus according to claim 14, wherein the collimator is a cone beam collimator with a single convergence point;

wherein the radiation source is a point=shaped radiation source, which is arranged adjacent to the convergence point of the collimator; and wherein said plane in which the radiation is radiated contains the convergence point of the collimator; and which means are present for rotating said plane about an axis of rotation lying in that plane, which axis of rotation intersects the convergence point of the collimator.

16. The apparatus according to claim 15, wherein the radiation-directing means comprises:

a shielding which is provided with a movable passage slit.

17. The apparatus according to claim 16, wherein the point-shaped radiation source is located substantially at the convergence point of the collimator;

wherein the shielding extends around the radiation source; and wherein the shielding is rotatable about the axis of rotation.

18. The apparatus according to claim 14, wherein the radiation source is stationarily arranged adjacent the focal point of the cone beam collimator; and wherein the radiation source is associated with a shielding element provided with a passage slit, the passage slit of said shielding element being movable with respect to the radiation source.

19. The apparatus according to claim 18, wherein the shielding element is a plate-shaped shielding element that is linearly movable in a direction perpendicular to said passage slit.

20. The apparatus according to claim 19, wherein the shielding element is a shielding element extending around the radiation source, which shielding element is rotatable about an axis of rotation extending through the radiation source, which axis of rotation is parallel to said passage slit.

21. The apparatus according to claim 14, wherein a first camera and a second camera are arranged at an angle with respect to each other, which angle is about 90°;

wherein the first camera is provided with a first cone beam collimator, whose focal point is located on the side of the first cone beam collimator directed to the second camera;

wherein the second camera is provided with a second cone beam collimator, whose focal point is located on the side of the second cone beam collimator directed to the first camera;

wherein adjacent the focal point of the first cone beam collimator a first point source is arranged, which is associated with a first shielding element with a first movable passage slit; and wherein adjacent the focal point for the second cone beam collimator a second point source is arranged, which is associated with a second shielding element with a second movable passage slit;

wherein the first passage slit and the second passage slit are mutually parallel; and wherein the first passage slit is movable in a direction perpendicular to the fist passage slit, and wherein the second passage slit is movable in a direction perpendicular to the second passage slit.

22. The apparatus according to claim 18, wherein the shielding element is arranged before the radiation source, which shielding element is provided with a substantially point-shaped passage opening, and wherein said point-shaped passage opening is located adjacent the focal point of a cone beam collimator.

23. An apparatus for making transmission and/or emission recordings of an object using radiation, the apparatus comprising:

a radiation source;

a camera sensitive to radiation from the radiation source and to emitted radiation from the object, the radiation and the emitted radiation having different energy levels;

a collimator arranged between the radiation source and the camera;

radiation-directing means which ensure that the radiation of the radiation source is radiated in a planar radiation beam so that the camera is illuminated according to a substantially line-shaped irradiation pattern; and means for moving the line-shaped irradiation pattern over the camera in a direction substantially perpendicular to the longitudinal direction thereof;

wherein the collimator is fixed relative to the camera; and wherein the collimator is a focused cone beam collimator.

* * * * *

UNITED STATES PATENT AND TRADEMARK OFFICE
CERTIFICATE OF CORRECTION

PATENT NO. : 6,324,258 B1
DATED : November 27, 2001
INVENTOR(S) : Federick Johannes Beekman It is certified that error appears in the above-identified patent and that said Letters Patent is hereby corrected as shown below:

Column 12,
Line 58, delete "claim 2", insert -- claim 3 --
Line 65, delete "claim 2, insert -- claim 3 --

Signed and Sealed this

Twenty-eighth Day of May, 2002

Attest:

JAMES E. ROGAN
Attesting Officer    Director of the United States Patent and Trademark Office